(12) United States Patent
Dall'Asta et al.

(10) Patent No.: US 6,365,747 B1
(45) Date of Patent: Apr. 2, 2002

(54) METHOD FOR THE PREPARATION OF CITALOPRAM

(75) Inventors: Leone Dall'Asta, Pavia; Umberto Casazza, Turate, both of (IT); Hans Petersen, Vanløse (DK)

(73) Assignee: H. Lundbeck A/S, Valby-Copenhagen (DK)

( * ) Notice: Subject to any disclaimer, the term of this patent is extended or adjusted under 35 U.S.C. 154(b) by 0 days.

(21) Appl. No.: 09/830,109

(22) PCT Filed: Oct. 19, 1999

(86) PCT No.: PCT/DK99/00576

§ 371 Date: Jun. 1, 2001

§ 102(e) Date: Jun. 1, 2001

(87) PCT Pub. No.: WO00/23431

PCT Pub. Date: Apr. 27, 2000

(30) Foreign Application Priority Data

Oct. 20, 1998 (IT) .......................................... MI98A2242
May 25, 1999 (IT) .......................................... MI99A1152
Aug. 2, 1999 (IT) .......................................... MI99A1724

(51) Int. Cl.$^7$ .................... C07D 307/87; C07D 413/10; C07D 417/10

(52) U.S. Cl. ........................ 548/146; 548/147; 548/201; 548/216; 548/238; 549/467

(58) Field of Search .......................... 549/467; 548/146, 548/147, 201, 216, 238

(56) References Cited

U.S. PATENT DOCUMENTS

| 3,467,675 A | 9/1969 | Petersen et al. | 260/346.2 |
|---|---|---|---|
| 4,136,193 A | 1/1979 | Bøgesø et al. | 424/285 |
| 4,650,884 A | 3/1987 | Bogeso | 549/467 |
| 6,020,501 A | 2/2000 | Massonne et al. | 549/307 |
| 6,028,204 A | 2/2000 | Massonne et al. | 549/307 |
| 6,229,026 B1 | 5/2001 | Petersen | 549/467 |
| 6,258,842 B1 | 7/2001 | Petersen et al. | 514/469 |
| 6,291,689 B1 | 9/2001 | Petersen et al. | 549/467 |

FOREIGN PATENT DOCUMENTS

| EP | 171 943 B1 | 1/1986 | C07C/121/80 |
|---|---|---|---|
| EP | 1 095 926 A2 | 5/2001 | C07C/33/46 |
| WO | 99/30548 | 6/1999 | |
| WO | 00/12044 | 3/2000 | |
| WO | 00/39112 | 7/2000 | C07D/307/87 |
| WO | 00/44738 | 8/2000 | C07D/307/88 |

OTHER PUBLICATIONS

U.S. Patent application Ser. No. 09/917,180, filed Jan. 26, 2000.
U.S. Patent application Ser. No. 09/977,920, filed Apr. 14, 1999.
U.S. Patent application Ser. No. 09/692,653, filed Oct. 19, 2000.
U.S. Patent application Ser. No. 09/794,762, filed Feb. 26, 2001.
U.S. Patent application Ser. No. 09/794,755, filed Feb. 26, 2001.
U.S. Patent application Ser. No. 09/888,067, filed Dec. 22, 1999.
U.S. Patent application Ser. No. 09/891,874, filed Oct. 25, 1999.

*Primary Examiner*—Bernard Dentz
(74) *Attorney, Agent, or Firm*—Darby & Darby

(57) ABSTRACT

The present invention relates to a method for the preparation of citalopram or any of its enantiomers and acid addition salts thereof comprising treatment of a compound of formula (IV), wherein X is O or S; $R^1$-$R^2$ are each independently selected from hydrogen and $C_{1-6}$ alkyl, or $R^1$ and $R^2$ together form a $C_{2-5}$ alkylene chain thereby forming a spiro-ring; $R^3$ is selected from hydrogen and $C_{1-6}$ alkyl, $R^4$ is selected from hydrogen, $C_{1-6}$ alkyl, a carboxy group or a precursor group therefore, or $R^3$ and $R^4$ together form a $C_{2-5}$ alkylene chain thereby forming a spiro-ring, with a dehydration agent or alternatively where X is S, thermally cleavage of the thiazoline ring, or treatment in presence of a radical initiator, to form citalopram. The invention also relates to intermediates used in the new process for the preparation of citalopram, as well as citalopram prepared according to the new process.

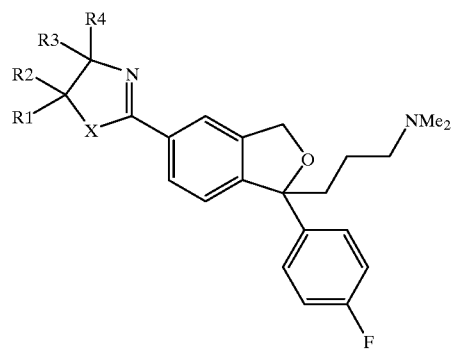

(IV)

17 Claims, No Drawings

METHOD FOR THE PREPARATION OF CITALOPRAM

The present invention relates to a method for the preparation of the well known antidepressant drug citalopram, 1-[3-(dimethylamino)propyl]-1-(4-fluorophenyl)-1,3-dihydro-5-isobenzofurancarbonitrile.

BACKGROUND OF THE INVENTION

Citalopram is a well-known antidepressant drug that has now been on the market for some to years and has the following structure:

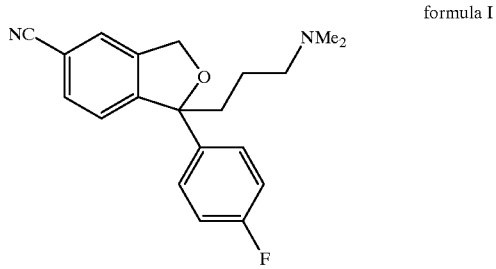

formula I

It is a selective, centrally acting serotonin (5-hydroxytryptamine; 5-HT) reuptake inhibitor, having antidepressant activities. The antidepressant activity of the compound has been reported in several publications, e.g. J. Hyttel, Prog. Neuro-Psychopharmacol. & Biol. *Psychiat.*, 1982, 6, 277–295 and A. Gravem, Acta Psychiatry. Scand., 1987, 75, 478–486. The compound has also been disclosed to show effects in the treatment of dementia and cerebrovascular disorders, EP-A 474580.

Citalopram was first disclosed in DE 2,657,271 corresponding to U.S. Pat. No. 4,136,193. This patent publication describes the preparation of citalopram by one method and outlines a further method that may be used for preparing citalopram.

According to the process described, the corresponding 1-(4-fluorophenyl)-1,3-dihydro-5-isobenzofurancarbonitrile is reacted with 3-(N,N-dimethylamino)propyl-chloride in the presence of methylsulfinylmethide as condensing agent. The starting material was prepared from the corresponding 5-bromo derivative by reaction with cuprous cyanide.

According to the second method, which is only outlined in general terms, citalopram may be obtained by ring closure of the compound:

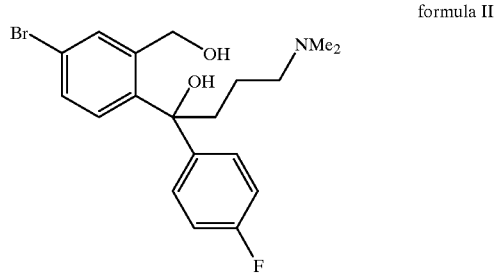

formula II in the presence of a dehydrating agent and subsequent exchange of the 5-bromo group with cyano using cuprous cyanide. The starting material of formula II is obtained from 5-bromophthalide by two successive Grignard reactions, i.e. with 4-fluorophenyl magnesium chloride and N,N-dimethylaminopropyl magnesium chloride, respectively.

A new and surprising method and an intermediate for the preparation of citalopram were described in U.S. Pat. No. 4,650,884 according to which an intermediate of the formula

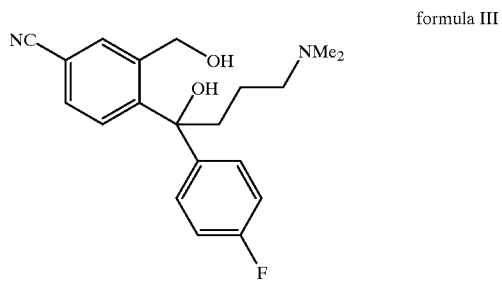

formula III is subjected to a ring closure reaction by dehydration with strong sulfuric acid in order to obtain citalopram. The intermediate of formula III was prepared from 5-cyanophthalide by two successive Grignard reactions, i.e. with 4-fluorophenyl magnesium halogenide and N,N-dimethylaminopropyl magnesium halogenide, respectively.

Further processes are disclosed in International patent application Nos. WO 98/019511, WO 98/019512 and WO 98/019513. WO 98/019512 and WO 98/019513 relate to methods wherein a 5-amino-, 5-carboxy- or 5-(sec. aminocarbonyl)phthalide is subjected to two successive Grignard reactions, ring closure and conversion of the resulting 1,3-dihydroisobenzofuran derivative to the corresponding 5-cyano compound, i.e. citalopram. International patent application No. WO 98/019511 discloses a process for the manufacture of citalopram wherein a (4-substituted-2-hydroxymethylphenyl-(4-fluorphenyl)methanol compound is subjected to ring closure and the resulting 5-substituted 1-(4-fluorophenyl)-1,3-dihydroisobenzofuran converted to the corresponding 5-cyano derivative and alkylated with a (3-dimethylamino)propylhalogenide in order to obtain citalopram.

Finally, methods of preparing the individual enantiomers of citalopram are disclosed in U.S. Pat. No. 4,943,590 from which it also appears that the ring closure of the intermediate of formula III may be carried out via a labile ester with a base.

It has now been found that citalopram may be obtained in a high yield as a very pure product by a new process in which an optionally substituted 2-[1-[3-(dimethylamino) propyl]-1-(4-fluorophenyl)-1,3-dihydroisobenzofuran-5-yl] oxazoline or -thiazoline is converted in one step to citalopram substantially without any occurrence of undesired side-reactions.

It has also been found that it is possible to prepare the optionally substituted 2-[1-[3-(dimethylamino)propyl]-1-(4-fluorophenyl)- 1,3-dihydroisobenzofuran-5-yl]oxazoline or -thiazoline intermediate directly starting from 5-carboxyphthalide, by formation of its amide with an optionally substituted 2-hydroxy-ethylamine or 2-mercapto-ethylamine and ring closure. The intermediate oxazolines and thiazolines are stable under the Grignard reaction conditions.

SUMMARY OF THE INVENTION

Accordingly, the present invention relates to a novel method for the preparation of citalopram, its enantiomers and acid addition salts thereof comprising treatment of a compound of formula IV formula IV

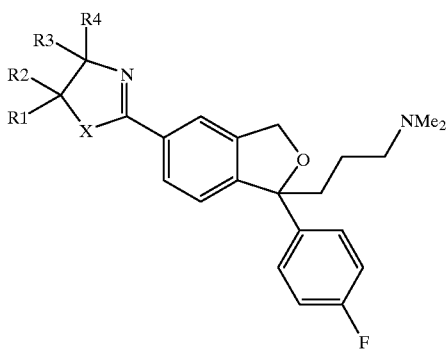

wherein X is O or S;

$R^1$-$R^2$ are each independently selected from hydrogen and $C_{1-6}$ alkyl, or $R^1$ and $R^2$ together form a $C_{2-5}$ alkylene chain thereby forming a spiro-ring; $R^3$ is selected from hydrogen and $C_{1-6}$ alkyl, $R^4$ is selected from hydrogen, $C_{1-6}$ alkyl, a carboxy group or a precursor group therefore, or $R^3$ and $R^4$ together form a $C_{2-5}$ alkylene chain thereby forming a spiro-ring; with a dehydration agent or alternatively where X is S, thermally cleavage of the thiazoline ring or treatment with a radical initiator, such as peroxide or with light, to form citalopram having the formula formula I

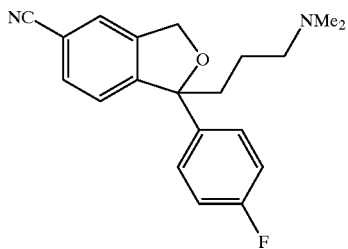

as the base or an acid addition salt thereof, and thereafter optionally converting said base or said acid addition salt to a pharmaceutically acceptable salt thereof.

The dehydration agent may be any suitable dehydration agent conventionally used in the art, such as phosphoroxytrichloride, thionylchloride, phosphorpentachloride, PPA (polyphosphoric acid), and $P_4O_{10}$. The reaction may be carried out in the presence of an organic base, such as pyridine.

Alternatively, the dehydration agent may be a Vilsmeier reagent, i.e. a compound which is formed by reaction of a chlorinating agent, preferably an acid chloride, e.g. phosgene, oxalyl chloride, thionyl chloride, phosphoroxychloride, phosphorpentachloride, trichloromethyl chloroformate, also briefly referred to as "diphosgene", or bis(trichloromethyl) carbonate, also briefly referred to as "triphosgene", with a tertiary amide such as N,N-dimethylformamide or a N,N-dialkylalkanamide, e.g N,N-dimethylacetamide. A classic Vilsmeyer reagent is the chloromethylenedimethyliminium chloride. The Vilsmeier reagent is preferably prepared in situ by adding the chlorinating agent to a mixture containing the starting oxazoline or thiazoline derivative of formula IV and the tertiary amide.

When X is S and the conversion of the thiazoline group into the cyano group is made by thermal transformation, the thermal decomposition of compound IV is preferably carried out in an anhydrous organic solvent, more preferably an aprotic polar solvent, such as N,N-dimethylformamide, N,N-dimethylacetamide, dimethylsulfoxide or acetonitrile. The temperature at which the thermal decomposition transforms the 2-thiazolyl group to a cyano group is between 60° C. and 140° C. The thermal decomposition may conveniently be carried out by reflux in a suitable solvent, preferably acetonitrile. The thermal cleavage may conveniently be carried out in the presence of oxygen or an oxidation agent. Compounds of formula IV where X is S and $R^4$ is a carboxy group or a precursor for a carboxy group can also be converted to citalopram by treatment with a radical initiator such as light or peroxides.

In a further aspect, the invention relates to the above process in which the compound of formula IV is in the form of the S-enantiomer.

In yet another aspect, the present invention relates to citalopram and S-citalopram manufactured by the process of the invention and an antidepressant pharmaceutical composition comprising citalopram or S-citalopram manufactured by the process of the invention.

According to the present invention, it has surprisingly been found that the oxazoline or thiazoline group may be introduced into the 5-position of phthalide and that remain stable during the subsequent reactions.

Furthermore, it has been found that the 1,1-disubstituted isobenzofurancarbonyl group in the intermediate of formula IV is surprisingly stable and that the reaction of the 2-[1-[3-(dimethylamino)propyl]-1-(4-fluorophenyl)-1,3-dihydroisobenzofuran-5-yl]oxazoline or -thiazoline with a dehydration reagent, in particular by a Vilsmeier reagent, to give the corresponding nitrile, i.e. citalopram, may be carried out at higher temperatures than those described in relation to such dehydration reactions in the literature.

It has also been found that, due to the combined stability of the optionally substituted 2-oxazolinyl or 2-thiazolinyl group and the 1,1-disubstituted isobenzofuranyl group, it is possible to prepare the 2-[1-[3-(dimethylamino)propyl]-1-(4-fluorophenyl)-1,3-dihydroisobenzofuran-5-yl]oxazoline or -thiazoline intermediate IV and, hence, citalopram and its salts in pure form, starting directly from 5-carboxyphthalide.

By the process of the invention, citalopram is obtained as a pure product in good yield thereby reducing costly purification processes.

According to the present invention, the compound of formula IV may be prepared from 5-carboxyphthalide and transformed to citalopram and its salts by a process, comprising:

a) reacting a functional derivative of 5-carboxyphthalide of formula V (V)

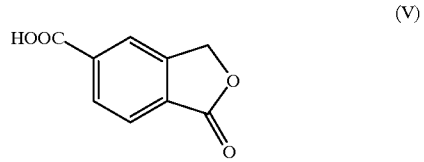

with a 2-hydroxy- or 2-mercaptoethanamine of formula VI

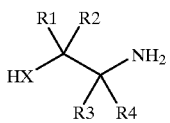

in which X, R$^1$–R$^4$ are as defined above, (b) submitting the amide of formula VII thus obtained

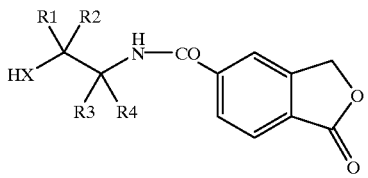

in which X, R$^1$–R$^4$ are as defined above, to a ring closure by dehydration;

(c) submitting the 2-(1-oxo-1,3-dihydroisobenzofuran-5-yl)oxazoline or -thiazoline of formula VIII thus obtained

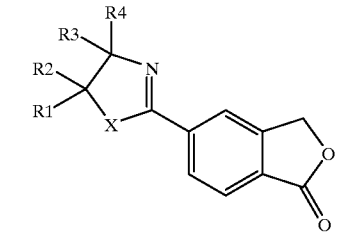

in which X, R$^1$–R$^4$ are as defined above, to two subsequent Grignard reactions, the first with a fluorophenyl magnesium halide and the second in situ with a [3-(dimethylamino)propyl]magnesium halide;

(d) submitting the 2-[3-hydroxymethyl-4-[(1-(4-fluorophenyl)-1-hydroxy-[4-(dimethylamino)butyl]phenyl]oxazoline of formula IX thus obtained

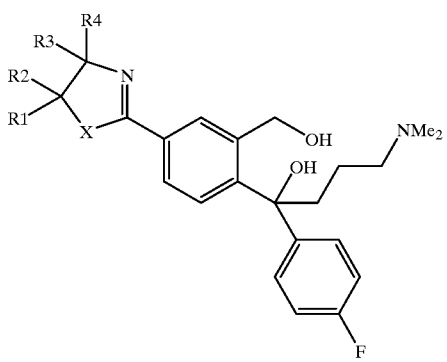

in which X, R$^1$–R$^4$ are as defined above, to a ring closure by dehydration;

(e) reacting the 2-[1-[3-(dimethylamino)propyl]-1-(4-fluorophenyl)-1,3-dihydroisobenzofuran-5-yl]oxazoline or -thiazoline thus obtained of formula IV

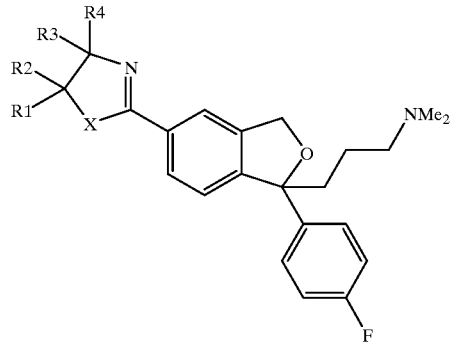

in which X, R$^1$–R$^4$ are as defined above, with a dehydration reagent or alternatively if X is S subjecting the compound of formula IV to a thermal decomposition reaction, or treatment with a radical initiator; and isolating the thus obtained citalopram in form of the free base or as an acid addition salt thereof; and (f) optionally converting said free base or said acid addition salt to a pharmaceutically acceptable salt thereof.

The total synthesis of citalopram as outlined above, comprises the use of novel intermediates for the preparation of the intermediary oxazolines or thiazolines by reaction of a 5-carboxyphthalide with an optionally substituted etanolamine or mercaptoethylamine and ring closure of the amide thus obtained.

The functional derivative of 5-carboxyphthalide used in step (a) is a acid halide thereof, the anhydride, a mixed anhydride, an active ester, for example the 4-nitrophenylester, or the free acid, suitably activated for example with dicyclohexylcarbodiimide. A preferred functional derivative is the acid chloride, which may be obtained by reaction of the free acid with thionyl chloride and straightforwardly made to react in situ with the 2-hydroxyethylamine or 2-mercapto ethylamine of formula VI. The 5-carboxyphthalide can be prepared from 5-cyanophthalide.

Another advantageous functional derivative is the mixed anhydride with a monoester of carbonic acid, preferably with carbonic acid monoethylester, which may be obtained from 5-carboxyphthalide and ethyl chloroformate and directly made to react in situ with the 2-hydroxy-ethylamine or 2-mercapto ethylamine of formula VI.

In the starting material of formula VI, R$^1$–R$^4$ are preferably selected from methyl or ethyl or hydrogen or one of the pairs of R$^1$ and R$^2$ or R$^3$ and R$^4$, respectively, are linked in order to form a 1,4-butylene or a 1,5-pentylene group. Most preferably, R$^1$ and R$^2$ and R$^3$ and R$^4$, respectively, are identical. The preferred reagents are 2-amino-2-methyl-1-propanol, 2-amino-2-methyl-1-propanthiol, 2-amino-3-hydroxy-propionic acid (R,S-serine, R-serine, and S-serine) and R,S-cysteine, R-cysteine and S-cysteine. The compounds of formula VI are commercially available or may be prepared from commercially available compounds using conventional methods.

The reaction of the functional derivative of 5-carboxyphthalide (V) with the ethanolamine or mercaptoethylamine VI is carried out at a temperature of 10–40° C., preferably at 15–25° C., in an aprotic organic solvent such as an ether, for example methyl t-butyl ether, tetrahydrofuran or dioxane, a ketone, for example acetone or methylisobutylketone, a hydrocarbon, for example toluene, or a chlorinated solvent, for example dichloromethane, 1,2-dichloroethane or 1,1,1-trichloroethane. Preferably, a hydrocarbon, conveniently toluene, is used when the functional derivative is the chloride, whereas a ketone, conveniently acetone, is used when the functional derivative is a mixed anhydride. The reaction occurs in the usual manner of formation of the amides. However, when the activated acid derivative is the 5-carboxy phthalide chloride, the reaction is conveniently carried out in the presence of an inorganic base such as sodium or potassium carbonate, whereas an organic base such as triethylamine may be employed when, for example, the mixed anhydride with carbonic acid monoethylester is used as functional derivative.

In step (b), the amide of formula VII is submitted to a ring closure reaction by dehydration, preferably by treatment with thionyl chloride. The amide of formula V is added to the dehydration agent at low temperature, namely at less than 10° C., preferably less than 5° C., most preferred between −10° C. and 3° C. When thionyl chloride is used, the temperature is advantageously less than 0° C., preferably about −10° C. Then the temperature is allowed to rise to 20° C. and the reaction is completed at a temperature of 20–40° C., preferably at 25–35° C., most preferred at 28 to 30° C.

When thionyl chloride is used as the dehydrating agent the 2-(1-oxo-1,3-dihydroisobenzofuran-5-yl)oxazoline or -thiazoline of formula VIII is obtained in the form of a hydrocloride which may be isolated by dilution with an etheric solvent, preferably tetrahydrofuran. The corresponding base may be isolated by precipitation from an aqueous alkaline solution of the hydrochloride.

The above steps (a) and (b) can be carried out as a one-pot process, namely without isolating the amide of formula VII.

In step (c), the compound of formula VIII thus obtained is submitted to two subsequent Grignard reactions. In particular, it is reacted under usual conditions with a 4-fluorophenyl magnesium halide, conveniently the chloride or the bromide, preferably the bromide, and preferably using tetrahydrofuran as solvent. The reaction mixture is then treated with a [3-(dimethylamino)propyl] magnesiumhalogenide, conveniently the chloride or bromide, preferably the chloride, dissolved in the same solvent used for the previous Grignard reaction, preferably tetrahydrofuran, using the usual conditions of a Grignard reaction.

The 2-[3-hydroxymethyl-4-[(1-(4-fluorophenyl)-1-hydroxy-[4-(dimethylamino)butyl]phenyl]oxazoline or -thiazoline of formula IX thus obtained may be isolated according to the conventional techniques.

In step (d), ring closure of compound IX is carried out through elimination of a molecule of water. This elimination may be effected by an acid or via a labile ester with a base. Acidic ring closure is performed with an inorganic acid, such as a sulfuric or phosphoric acid, or an organic acid, such as methylsulfonic, p-toluenesulfonic or trifluoroacetic acid. The basic ring closure is performed via a labile ester, such as the methane sulfonyl, p-toluene sulfonyl, 10-camphorsulfonyl, trifluoroacetyl or trifluoromethanesulfonyl ester in presence of a base, such as triethyl amine, dimethylaniline, pyridine, etc. The reaction is performed in an inert solvent, preferably with cooling, in particular about 0° C. and is preferably carried out by a one-pot procedure, i.e. with esterification in presence of a base.

Step (e), the treatment of the compound of IV with the dehydrating reagent is carried out as described above. The reaction of the compound of formula IV, as the free base or as a salt thereof, with the Vilsmeier reagent is carried out in anhydrous organic solvent. The anhydrous organic solvent may be an apolar solvent such as a hydrocarbon, e.g toluene or xylene, or a polar solvent, or it may be the N,N-dimethylformamide or N,N-dimethylacetamide which form the Vilsmeier reagent, wherein the tertiary amide is present in at least the stoechiometrical amount in respect of the acid chloride, preferably in an excess thereof, e.g in a double amount of the stoechiometrical amount. Addition of the clorinating agent is generally made at low temperatures, but the reaction itself occurs at a temperature of from 80–150° C., preferably 90–130° C., or more preferred 100–120° C. These temperature ranges allow the reaction to be completed within 4 hours, particularly within 30–60 minutes.

Ring closure in step d) and subsequent dehydration in order to convert oxazoline or thiazoline to CN in step e) may in a preferred embodiment be performed in one step without isolation of the intermediate of formula IV, e.g. by using thionylchloride as dehydration agent.

As set forth above, the citalopram thus obtained may be isolated in form of free base or of a salt thereof and converted to the selected final product, preferably citalopram hydrobromide.

The process of the present invention allows the preparation of citalopram and of its salts starting from compounds carrying an oxazoline or thiazoline groups which represent valuable and direct precursors of the cyano group which are stable under the conditions of a Grignard reaction. Thermal decomposition of the oxazoline or thiazoline groups in the compound of formula IV may be very simple and convenient.

Moreover, the process of the present invention allows the preparation of two the enantiomers of citalopram and of their salts starting from the corresponding enantiomers of the compound of formula IV or, when using the total synthesis starting from 5-carboxy phthalide, by resolution of the compound of formula IX. Compounds of formula IV or IX, in which $R^3$ and $R^4$ represent methyl and $R^1$ and $R^2$ are hydrogen, are particularly indicated.

The intermediates of formula IV and IX in the form of enantiomers, may be obtained using conventional separation techniques or as describe in U.S. Pat. No. 4.943.590.

It is advantageous to treat the compounds of formula IX as racemate, with an optically active acid, for example with (−)- or (+)-tartaric acid or (−)- or (+)-camphor-10-sulfonic acid, in order to separate the diastereoisomeric salt mixture and to isolate the optically active compound of formula IX, as free base or as a salt thereof.

The total synthesis of citalopram and of its salts directly from 5-carboxyphthalide, represents a preferred embodiment, and involves a series of intermediates which are a further object of the present invention.

Thus, according to another of its objects, the invention relates to the compounds of formula IV obtainable according to step (d) and the compounds of formula VIII and IX obtained according to step (b) and (c).

The salts of the compounds IV, VIII and IX may be any acid addition salt, including pharmaceutically acceptable acid addition salts, for example the hydrochloride, hydrobromide, hydrogen.

Other reaction conditions, solvents, etc. are conventional conditions for such reactions and may easily be determined by a person skilled in the art.

The compound of general formula I may be used as the free base or as a pharmaceutically acceptable acid addition salt thereof. As acid addition salts, such salts formed with organic or inorganic acids may be used. Exemplary of such organic salts are those with maleic, fumaric, benzoic, ascorbic, succinic, oxalic, bismethylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, benzene sulfonic and theophylline acetic acids, as well as the 8-halotheophyllines, for example 8-bromotheophylline. Exemplary of such inorganic salts are those with hydrochloric, hydrobromic, sulfuric, sulfamic, phosphoric and nitric acids.

The acid addition salts of the compounds may be prepared by methods known in the art. The base is reacted with either the calculated amount of acid in a water miscible solvent, such as acetone or ethanol, with subsequent isolation of the salt by concentration and cooling, or with an excess of the acid in a water immiscible solvent, such as ethylether, ethylacetate or dichloromethane, with the salt separating spontaneously.

The pharmaceutical compositions of the invention may be administered in any suitable way and in any suitable form, for example orally in the form of tablets, capsules, powders or syrups, or parenterally in the form of usual sterile solutions for injection.

The pharmaceutical formulations of the invention may be prepared by conventional methods in the art. For example, tablets may be prepared by mixing the active ingredient with ordinary adjuvants and/or diluents and subsequently compressing the mixture in a conventional tabletting maschine. Examples of adjuvants or diluents comprise: Corn starch, potato starch, talcum, magnesium stearate, gelatine, lactose, gums, and the like. Any other adjuvant or additive colourings, aroma, preservatives etc. may be used provided that they are compatible with the active ingredients.

Solutions for injections may be prepared by solving the active ingredient and possible additives in a part of the solvent for injection, preferably sterile water, adjusting the solution to the desired volume, sterilisation of the solution and filling in suitable ampoules or vials. Any suitable additive conventionally used in the art may be added, such as tonicity agents, preservatives, antioxidants, etc.

The invention is further illustrated by the following examples:

EXAMPLE 1

Preparation of Citalopram Hydrobromide

To a mixture of 4,4-dimethyl-2-[1-[3-(dimethyl amino) propyl]-1-(4-fluorophenyl)-1,3-dihydroisobenzofuran-5-yl] oxazoline (19 g, 0.0479 mol) in N,N-dimethylformamide (50 ml), cooled to −20° C., there are added 8.93 ml of $POCl_3$ (0.0958 m), without allowing the temperature to rise above −10° C. At the end of the addition, the temperature is allowed to rise to 10–15° C., then the mixture is heated at 110–115° C. for 45–60 minutes and thereafter immediately cooled to 20–25° C. The mixture is treated with 80 ml of deionized water and pH is adjusted to 9 by addition of a concentrated solution of ammonium hydroxide. The product is deeply extracted with toluene, by carrying out the operation four times with 80, 60, 50 and, respectively, of toluene (40 ml), then the organic phases are collected and decolourised by treatment with charcoal for 30 minutes. The charcoal is filtered off and the solvent is evaporated leaving 13.5 g of an oil. The oily residue is taken up with 80 ml of acetone and the obtained solution is treated with of a 48% HBr (4 ml) solution. The mixture thus obtained is concentrated in vacuo, and the oily residue is taken up with of acetone (40 ml) and the solution is allowed to stand overnight at 4–5° C. The solid is filtered off, washed at the first with toluene, then with acetone and dried. Thus, 9.4 g of citalopram hydrobromide is obtained.

The mother liquors are concentrated to dryness, the residue is taken up with 20 ml of acetone, the solution is kept 4 hours at 4–5° C., then it is filtered, washed with a little amount of acetone and dried. Thus, there is obtained a further 1.44 g of citalopram hydrobromide.

EXAMPLE 2

Synthesis of Citalopram Hydrobromide Starting from 5-carboxyphtalide (a) 2-[[(1-Oxo-1,3-dihydroisobenzofuran-5-yl)carbonyl] amino]-2-methyl-1-propanol To a stirred mixture of thionyl chloride (1850 ml) and N,N-dimethylformamide (5.5 ml), 5-carboxyphthalide (525 g, 2.95 mol) is added. The stirred mixture is heated at reflux for 6 hours. The thionyl chloride is distilled off under reduced pressure to give the acid chloride as the residue. The residue is taken up in toluene (750 ml) and concentrated under reduced pressure. The residue is taken up in toluene (2×450 ml), concentrated under reduced pressure, then taken up in tetrahydrofuran (2500 ml).

To a solution of 2-amino-2-methyl-1-propanol (800 g, 8.97 mol) in tetrahydrofuran (1300 ml) at 5° C., the solution of the acid chloride is added dropwise, maintaining the temperature between 5–10° C. Then the mixture is stirred at about 20° C. for 2 hours. It is controlled that the mixture is alkaline and then the solvent is evaporated in vacuo at 50° C. The residue is taken up in deionized water (2400 ml) and stirred for one hour. The solid product is isolated by filtration and washed with deionized water. The product is dried at 50° C. in vacuo. Yield: 570 g (77%) having m.p.=156–158° C. and purity (HPLC, peak area)≧90%.

(b) 4,4-Dimethyl-2-(1-oxo-1,3-dihydroisobenzofuran-5-yl) oxazoline

To stirred thionyl chloride (800 ml), at 0° C., 2-[[(1-oxo-1,3-dihydroisobenzofuran-5-yl)carbonyl]amino]-2-methyl-1-propanol (560 g, 2.25 mol) is added portionwise while maintaining the temperature below 10° C. The temperature is allowed to rise, and then the mixture is heated between 28–30° C. for 5 hours. The thionyl chloride is destined off under reduce pressure at 60° C. The residue is taken up in toluene (2×700 ml) and concentrated under reduce pressure at 60° C. The solid is filtered off, washed with toluene (2×100 ml) and dried at in vacuo. The product is suspended in deionized water (3000 ml). The suspension is cooled and pH is adjusted to basic pH by addition of 28% aqueous ammonia (1000 ml). The product is filtered off, washed with deionized water, and dried at 50° C. in vacuo. Yield: 407 g (78%) having m.p.=109–111° C. and purity (HPLC, peak area)≧95%.

(c) 4,4-Dimethyl-2-[3-hydroxymethyl-4-[4-fluoro-α-hydroxy-α-(dimethylamino)propyl]benzyl]phenyl] oxazoline Under an atmosphere of nitrogen a solution of 4,4-dimethyl-2-(1-oxo-1,3-di hydroisobenzofuran-5-yl) oxazoline (135 g, 0.58 mol) (obtained from step (b)), in tetrahydrofuran (900 ml), is stirred at −15° C. Then a 20% solution of p-fluorophenylmagnesium bromide in tetrahydrofuran (1130 g) is slowly added while maintaining the temperature between −15 to −10° C. The temperature is allowed to rise to 5–10° C. and maintained at 5–10° C. for 1 hr. A control by HPLC is made to verify that the amount of starting material is lower than 1% (area). Then the stirred solution is cooled to −5° C. and a 30% solution of (3-(dimethylamino)propyl) magnesium chloride in tetrahydrofuran (430 g) is added slowly while maintaining the temperature between −5° C. and −2° C. The temperature is allowed to rise to 5–10° C. and kept and maintained at 5–10°

C. for 1 hr. After a control by HPLC, showing that the residue of the reaction intermediate is less than 5% (area), a 15% aqueous solution of ammonium chloride (approx 1000 g) is slowly added and the mixture is stirred for 30 minutes. The phases are separated and the lower phase is extracted with toluene (1000+700 ml). Then deionized water (1050 ml) is added to the upper phase and the pH is adjusted to 5–6 by addition of acetic acid. The solvent is evaporated at 50° C. in vacuo and to the residual aqueous phase the toluene extracts are added. After cooling, the pH of the mixture is adjusted to 9–10 with 30% aqueous ammonia. The phases are separated and the aqueous phase is extracted with toluene (300 ml). The organic phases are combined and a mixture of acetic acid (660 ml) and of deionized water (1050 ml) is added thereto (final pH about 4.2). The phases are separated; the aqueous phase is recovered, treated with decolourising charcoal and filtered. To this filtered solution of toluene (1200 ml), the solution is cooled to 10–15° C. and pH of the suspension is adjusted pH 10 by addition of 30% of aqueous ammonia. The phases are separated and the aqueous phase is extracted with toluene (300 ml). The toluene phases are combined and washed with deionized water (150 ml). The product is allowed to crystallise at ambient temperature for three hours and thereafter at 5° C. for 15 hours. The product is filtered off and washed with anhydrous toluene. Yield: 154 g.

A further amount of 18 g of product is recovered from the mother liquors.

Total yield: 154+18 g (71%) with a purity (HPLC, peak area)≧95%.

(d) 4,4-Dimethyl-2-[1-[3-(dimethylamino)propyl]-1-(4-fluorophenyl)-1,3-dihydroisobenzofuran-5-yl]oxazoline To a stirred solution 4,4-dimethyl-2-[3-hydroxymethyl-4-[4-fluoro-α-hydroxy-α-[3-dimethylamino)propyl]benzyl]]oxazoline (141 g, 0.34 mol), (obtained at the end of step (c)) in methylene chloride (2200 ml), triethylamine (200 ml) is added. The stirred mixture is cooled to 5° C. and a solution of methanesulfonyl chloride (40 ml, 0.515 mol) in methylene chloride (400 ml) is added while maintaining the temperature between 5–7° C. The temperature is brought to 25° C. and the mixture is maintained under these conditions for 2 hours. The mixture is cooled and 0.1 N NaOH solution (1000 ml) is added. The phases are separated and the organic phase is washed with of deionized water (3×1000 ml). The organic phase is concentrated under reduced pressure at 50° C. resulting in an oily residue. Yield: 130 g (96%) with a purity (HPLC, peak area)≧85%.

(e) Citalopram Hydrobromide

To a stirred solution of 4,4-dimethyl-2-[1-[3-(dimethylamino)propyl]-1-(4-fluorophenyl)-1,3-dihydroisobenzofuran-5-yl]oxazoline (287 g, 0.724 mol) in pyridine (1000 ml), at 5° C., phosphorous oxychloride (135 ml, 1.474 mol) is slowly added while keeping the temperature at 5 to 10° C. The mixture is heated at reflux (115–116° C.) for 3 to 4 hours. The mixture is cooled to about 10° C. and treated with deionized water (3200 mL), and the pH is adjusted to about pH 9 by addition of 28% aqueous ammonia (800 ml). The product is extracted with of toluene (1500+1000+500+500 ml) and the combined organic phases are decoloured with charcoal. The organic phase is concentrated under reduced pressure at 60–70° C. to give an oily residue to which acetone (3000 ml) is added. The acetone solution is cooled to 10° C. and treated with 60 ml 48% HBr to a pH value of 4–5. The solvent is evaporated under reduced pressure and the residue is taken up in acetone (800 ml). The mixture is heated to 40–50° C. and thereafter cooled to 5° C. After 15 hours at 5° C. the product is filtered off, washed with cold acetone (500 ml) and dried in vacuo at 50° C. 175–180 g of citalopram hydrobromide with a purity (HPLC, peak area)≧90% is obtained.

A further amount of 15 g with a purity (HPLC, peak area)≧90% of product is recovered from the mother liquors.

Yield: 190–195 g (65–67%) with a purity (HPLC, peak area)≧90%

(f) Crystallization of Citalopram Hydrobromide

A mixture of raw citalopram hydrobromide (190 g) and deionized water (380 ml) is heated at 50–60° C. until all solid has been dissolved. The solution is treated with charcoal (12 g), filtered and washed with deionized water (50 ml). The filtered solution is cooled to 20° C. and stirred at ambient temperature for 5 hours and then at 5° C. for 15 hours. The crystals are filtered off, washed with cold water (200 ml) and dried in vacuo at 60° C. for four hours.

EXAMPLE 3

Preparation of Citalopram Oxalate

A stirred solution of 4,4-dimethyl-2-[1-[3-(dimethylamino)propyl]-1-(4-fluorophenyl)-1,3-dihydroisobenzofuran-5-yl]oxazoline (2.3 g, 0.0058 mol) in thionylchloride (20 ml) is heated at reflux for 3 hours. The organic phase is concentrated under reduced pressure and the residue is taken up in toluene (20 ml) and deionized water (20 ml) is added and the pH of the mixture is adjusted to about 9 by addition of aqueous NaOH (2 N). The phases are separated and the organic phase is collected and washed with deionized water (2×10 ml). T The organic phase is concentrated under reduced pressure to leaving an oily residue. 1.8 g. The oxalate salt is precipitated from acetone.

EXAMPLE 4

4,4-Dimethyl-2-(1-oxo-1,3-dihydroisobenzofuran-5-yl)oxazoline (one-pot method)

To a mixture of thionyl chloride (25 ml, 0.344 mol) and N,N-dimethylacetamide (0.2 ml), 5-carboxyphthalide (5 g, 0.028 mol) is added. The stirred mixture is heated 30 minutes at 60° C. and is then brought to reflux (about 80° C.) and kept under these conditions for 6 hours. The thionyl chloride is distilled off in vacuo to an inner temperature of about 90° C. The concentrated mixture is taken up with toluene (25 ml) and distilled in vacuo leaving a residue, which is taken up again twice with of toluene (10 ml) followed by concentration of the solution. The residual acid chloride is taken up with of tetrahydrofuran (25 ml) and the mixture is heated at 60° C. until a complete dissolution is obtained. The solution of the acid chloride in tetrahydrofuran is added dropwise to a mixture of micronized anhydrous potassium carbonate (5 g, 0.036 mol), 2-amino-2-methyl-1-propanol (3.06 ml, 0.032 mol) and of tetrahydrofuran (15 ml), cooled to about 0° C., keeping the temperature at 5–10° C. After about 30 minutes under these conditions, a control by HPLC is performed in order to verify the complete amide formation. The mixture is cooled to 0–3° C. and of thionyl chloride (2 ml, 0.027 mol) is added dropwise to the mixture. At the end of the addition, a control by HPLC confirms that the ring closure of the amide is completed. To the mixture, 50 ml of deionized water is slowly added at 5–10° C. The organic solvents are distilled off in vacuo and the pH is adjusted to 5 with 25% ammonia. The mixture is heated one hour at 50° C., then its temperature is let to decrease to about 20° C., kept at this value for 2 hours, then lowered to 10–15°

C. and the mixture is maintained under these conditions for one hour. The mixture is dispersed by stirring, then it is filtered, washed with water and dried in vacuo at 40° C. Yield: 3.87 g of product. Total yield: 59.8%.

EXAMPLE 5

4,4-Dimethyl-2-(1-oxo-1,3-dihydroisobenzofuran-5-yl)oxazoline (one-pot method)

Acetone (40 ml) is stirred and 5-carboxyphthalide (2 g ,0.01 1 mol) are added at about 20° C. The mixture is cooled to −10° C. and ethyl chloroformate (1.18 ml, 0.012 mol) is added. At the end of the addition, a solution of triethylamine (1.56 ml ,0.011 mol) in acetone (3.50 ml) is added keeping the temperature of the mixture at or below −10° C. The temperature of the mixture is allowed to rise to 10–13° C. and, after 30 minutes, it is brought to −10° C. and a solution of 2-amino-2-methyl-1-propanol (3.0 g ,0.034 mol) in acetone (5 ml) is quickly added to the mixture. The temperature is allowed to rise to 15–20° C., whereby the reaction is completed as it may be verified by HPLC. To the mixture thus obtained, cooled to −5° C., thionyl chloride (2.5 ml, 0.034 mol) is added, the temperature is allowed to rise to about 20° C. and after 30 minutes the ring closure is completed. The reaction mixture is concentrated in vacuo leaving a residue, which is treated with water (20 ml). The mixture is concentrated again and a further amount of water (10 ml) is added to the residue, the pH is made basic by addition of 25% ammonia and the mixture is cooled to 5° C. The product is filtered off, washed with water and dried in vacuo. Yield: 1.70 g. Total yield: 66.8%.

What is claimed is:

1. A method for the preparation of citalopram or any of its enantiomers and acid addition salts thereof comprising treatment of a compound of formula IV formula IV

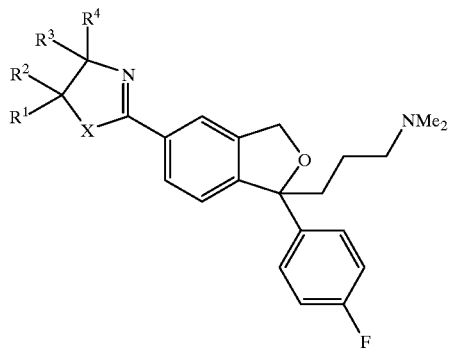

wherein X is O or S;

R$^1$-R$^2$ pendently selected from hydrogen and C$_{1-6}$ alkyl, or R$^1$ and R$^2$ together form a C$_{2-5}$ alkylene chain thereby forming a spiro-ring; R$^3$ is selected from hydrogen and C$_{1-6}$ alkyl, R$^4$ is selected from hydrogen, C$_{16}$ alkyl, a carboxy group or a precursor group therefore, or R$^3$ and R$^4$ together form a C$_{2-5}$ alkylene chain thereby forming a spiro-ring, with a dehydration agent or alternatively where X is S, thermally cleaving the thiazoline ring, or treatment in presence of a radical initiator, to form citalopram having the formula formula I

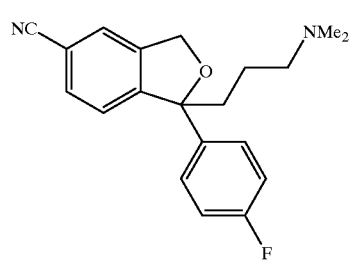

and thereafter optionally converting the free base or an acid addition salt thereof thus obtained to a pharmaceutically acceptable salt thereof.

2. A method according to claim 1 comprising:

a) reacting a functional derivative of 5-carboxyphthalide of formula V (V)

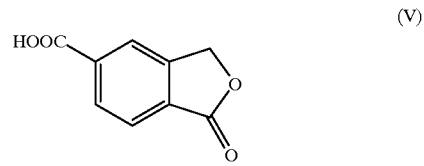

with a 2-hydroxy- or 2-mercaptoethanamine of formula VI (VI)

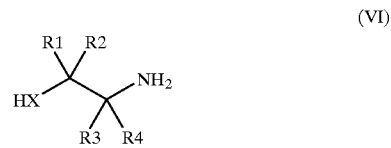

in which X, R$^1$–R$^4$ are as defined above, (b) submitting the amide of formula VII thus obtained (VII)

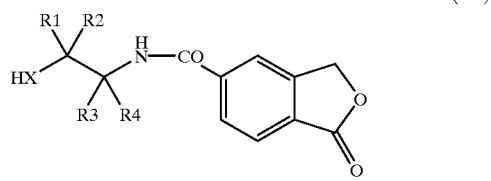

in which X, R$^1$–R$^4$ are as defined above, to a ring closure by dehydration;

(c) submitting the 2-(1-oxo-1,3-dihydroisobenzofuran-5-yl)oxazoline or -thiazoline of formula VIII thus obtained

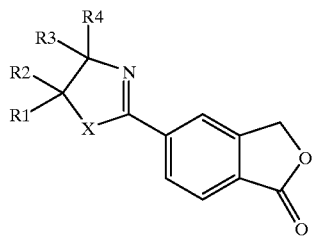

(VIII)

in which X, R¹–R⁴ are as defined above, to two subsequent Grignard reactions, the first with a fluorophenyl magnesium halide and the second in situ with a [3-(dimethylamino) propyl]magnesium halide;

(d) submitting the 2-[3-hydroxymethyl-4-[(1-(4-fluorophenyl)-1-hydroxy-[4-(dimethylamino)butyl] phenyl]oxazoline or -thiazoline of formula IX thus obtained

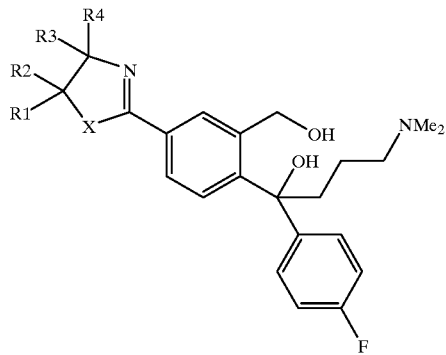

(IX)

in which X, R¹–R⁴ are as defined above, to a ring closure by dehydration;

(e) reacting the 2-[1-[3-(dimethylamino)propyl]-1-(4-fluorophenyl)-1,3-dihydroisobenzofuran-5-yl] oxazoline or -thiazoline thus obtained of formula IV

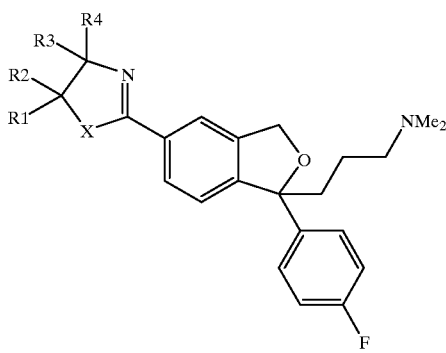

(IV)

in which X, R¹–R⁴ are as defined above, with a dehydration reagent or alternatively if X is S subjecting the compound of formula IV to a thermal decomposition reaction, or treatment with a radical initiator; and isolating the thus obtained citalopram in form of the free base or of a salt thereof; and (f) optionally converting the compound obtained into pharmaceutically acceptable salt thereof.

3. A method for the preparation of citalopram according to claim 1 or 2 wherein the compound of formula IV is treated with a dehydrating agent selected from phosphoroxytrichloride, thionylchloride, phosphorpentachloride, PPA (polyphosphoric acid) and P₄O₁₀ or a Vilsmeier reagent.

4. A method according to claim 3 wherein the Vilsmeier reagent is formed by reaction of a chlorinating reagent with a tertiary amide.

5. A method according to claim 4 wherein the clorinating agent is an acyl chloride selected from phosgene, oxalyl chloride, thionyl chloride, phosphoroxychloride, phosphorpentachloride and trichloromethyl chloroformate and the tertiary amide is selected from N,N-dimethylformamide or a N,N-dialkylalkanamide.

6. A method according to claim 3 wherein the Vilsmeier reagent is prepared in situ by adding the chlorinating agent to a mixture containing the starting oxazoline or thiazoline derivative of formula IV and the tertiary amide.

7. A method for the preparation of citalopram according to claim 1 or 2 wherein the thermal cleavage of the thiazoline ring of a compound of formula IV where X is S is carried out in presence of oxygen or an oxidizing agent.

8. A method for the preparation of citalopram according to claim 1 wherein the thiazoline ring of a compound of formula IV where X is S and R⁴ is carboxy or a precursor for carboxy is treated with a radical initiator.

9. A method according to claim 2 wherein step b) is carried out by subjecting the amide of formula VII to a ring closure reaction by dehydration.

10. A method according to claim 1 wherein the compound of formula IV is in the form of the S-enantiomer.

11. A method according to claim 2 wherein the compound of formula IX used is in the form of the S-enantiomer.

12. A compound of the general formula VIII or any of its enantiomers and acid addition salts thereof having the formula

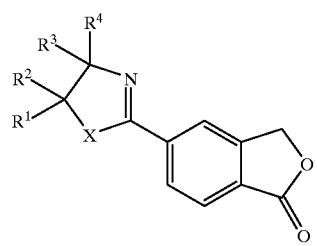

(VIII)

wherein X is O or S;

R¹-R² are each independently selected from hydrogen and C₁₋₆ alkyl, or R¹ and R² together form a C₂₋₅ alkylene chain thereby forming a spiro-ring; R³ is selected from hydrogen and C₁₋₆ alkyl R⁴ is selected from hydrogen, C₁₋₆ alkyl, a carboxy group or a precursor group therefore, or R³ and R⁴ together form a C₂₋₅ alkylene chain thereby forming a spiro-ring.

13. A compound of the general formula IX or any of its enantiomers and acid addition salts thereof having the formula

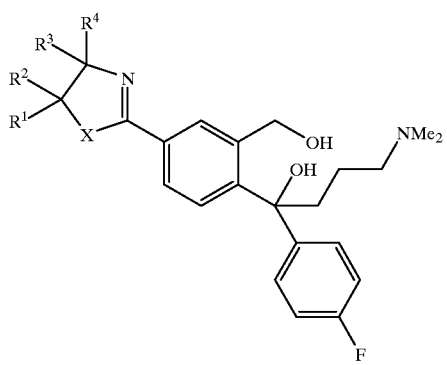

(IX)

wherein X is O or S;

$R^1$-$R^2$ are each independently selected from hydrogen and $C_{1-6}$ alkyl, or $R^1$ and $R^2$ together form a $C_{2-5}$ alkylene chain thereby forming a spiro-ring; $R^3$ is selected from hydrogen and $C_{1-6}$ alkyl, $R^4$ is selected from hydrogen, $C_{1-6}$ alkyl, a carboxy group or a precursor group therefore, or $R^3$ and $R^4$ together form a $C_{2-5}$ alkylene chain thereby forming a spiro-ring.

14. A compound of the general formula IV or any of its enantiomers and acid addition salts thereof having the formula

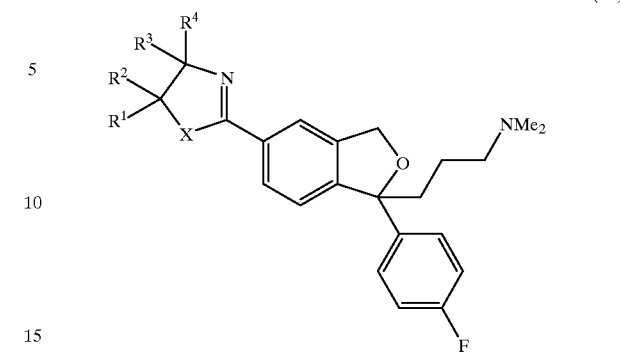

(IV)

wherein X is O or S;

$R^1$-$R^2$ are each independently selected from hydrogen and $C_{1-6}$ alkyl, or $R^1$ and $R^2$ together form a $C_{2-5}$ alkylene chain thereby forming a spiro-ring; $R^3$ is selected from hydrogen and $C_{1-6}$ alkyl, $R^4$ is selected from hydrogen, $C_{1-6}$ alkyl, a carboxy group or a precursor group therefore, or $R^3$ and $R^4$ together form a $C_{2-5}$ alkylene chain thereby forming a spiro-ring.

15. The method according to claim 2 wherein steps a) and b) are carried out as a one-pot process.

16. A method according to claim 9, wherein said step of dehydration comprises treatment with thionyl chloride at less than 10° C., and thereafter the temperature is allowed to rise to 20° C. and the reaction is completed at a temperature of 20–40° C.

17. A method according to claim 16 wherein said step of dehydration comprises treatment with thionyl chloride at less than 0° C.

\* \* \* \* \*